United States Patent [19]

Warriner

[11] Patent Number: Plant 6,668

[45] Date of Patent: Mar. 14, 1989

[54] ROSE PLANT JACBOR

[75] Inventor: William A. Warriner, Tustin, Calif.

[73] Assignee: Jackson & Perkins Company, Medford, Oreg.

[21] Appl. No.: 87,252

[22] Filed: Aug. 18, 1987

[51] Int. Cl.[4] ..... A01H 5/00

[52] U.S. Cl. ..... Plt./17

[58] Field of Search ..... Plt./16, 17, 20, 21

*Primary Examiner*—James R. Feyrer

*Attorney, Agent, or Firm*—Majestic, Gallagher, Parsons & Siebert

[57] ABSTRACT

A rose variety of the hybrid tea class is provided having a unique flower color for the blooms near Red Group 42B to 42D with large and small prickles on lateral stems, prickles and glands on petioles, seven leaflet leaves, and a reddish strip on otherwise green styles.

1 Drawing Sheet

SUMMARY OF THE INVENTION

The present invention relates to a new and distinct variety of rose plant of the hybrid tea class, which was originated by me by crossing the variety Flower World, U.S. Plant Pat. No. 4,576, with an unnamed seedling.

The primary objective of this breeding was to produce a new rose variety of the hybrid tea class with the flower color in Red Group 42 on a vigorous plant. This objective was substantially achieved, along with other desirable improvements, as evidenced by the following unique combination of characteristics which are outstanding in the new variety and which distinguish it from its parents as well as from all other varieties of which I am aware. For example, this new rose variety has:

1. Continuously produced flowers of Red Group 42B to 42C color;
2. Large and small prickles on lateral stems;
3. Prickles and glands on petioles;
4. Seven leaflet leaves;
5. Reddish strip on greenish style;
6. Vigorous upright growth habit.

Asexual reproduction of this new variety by budding, as performed at Wasco, Calif., shows that the foregoing characteristics and distinctions come true to form and are established and transmitted through succeeding propagation.

DESCRIPTION OF THE DRAWING

The accompanying illustration shows typical specimens of the vegetative growth and flowers of this new variety in different stages of development, depicted in color as nearly true as it is reasonably possible to make the same in a color illustration of this character.

DETAILED DESCRIPTION OF THE INVENTION

The following is a detailed description of my new rose cultivar, which has been denominated "Jacbor". Color terminology is in accordance with The Royal Horticultural Society Colour Chart except where an ordinary dictionary significance for the color is apparent.

Observations of the buds and flowers were made from specimens grown in a garden at Irvine, Calif. in July.

Flower

The blooming habit is continuous. The bud size is one and one-half inches when the petals start to unfurl. The bud form is pointed ovoid. The bud color when sepals first divide is near Red Group 42B; when half blown, the upper side of petals is near Red Group 42C, and the lower side of petals is near Red Group 42C. The sepals have a color near Green Group 138B. The surface texture is covered with fine hairs and glands. There are three normally appendaged, and two unappendaged sepals appendaged sepals with a hairy edge and an occasional gland. The receptacle color is green with a bronze cast and a funnel shape, medium size and smooth surface. The peduncle is medium, and has a glandular surface. Peduncle color is bronzy and the penduncle is stiff, erect and heavy.

Bloom

Bloom size is medium, with an average open size of four and one-half inches, borne singly and several together. The stems are strong and medium in length. The form when first open is high center. The petals then flatten and the outer petal edges are slightly curled. Under normal conditions there are 20 to 25 petals. The upper side of petals is near Red Group 42C, and the reverse side of the petals is near Red Group 42C. The base of petals has a small cream-colored half-moon at the point of attachment to the peduncle with the major color being near Red Group 42C. There are no variegations. The general tonality of the end of the first day shows no change in color. At the end of the third day, there is slight fading in bright sunlight to near Red Group 42D.

The fragrance is slight. The petal texture is thick, of a round to deltoid shape, and the form is flat with tips slightly recurved.

The arrangement is imbricated with no petaloids in the center. The blooms drop off cleanly, and last on the plant for a long period and as a cut flower for a long time.

Reproductive Parts

The anthers are medium and many, of reddish brown color, and arranged regularly around the styles. The filaments are reddish, the pollen is gold yellow, the styles are greenish with a distinctive red strip on each style, and the stigmas are greenish white.

Plant

A vigorous, upright growth of bush form.

Foliage

Medium size, normal in quantity. The new foliage is bronze colored that turns dark glossy green as old foliage. Normal mid-stem leaves have seven leaflets.

The leaflets are of an oval pointed shape, are leathery and glossy, and have a serrated edge. The serration is single and small in size. Petiole rachis is green, and petiole underside is rough with prickles and glands. Stipules are short and the edges are edged with glands. The foliage is susceptible to mildew under normal growing conditions at Irvine, Calif.

Wood

New wood is reddish, with a smooth bark. Old wood is green with a smooth bark.

Prickles

There are an ordinary number of prickles on main canes from the base and on laterals from the main canes.

The form is hooked downward. Color when young is red.

Small Prickles

There are few to no small prickles on the main stalks. The laterals have many small red prickles.

Parentage

The seed parent was the variety Flower World, U.S. Plant Pat. No. 4,576. The pollen parent was an unnamed seedling.

Classification

Botanical is rosa hybrid. Commercial is hybrid tea.

I claim:

1. A new and distinct variety of rose plant and parts thereof of the hybrid tea class substantially as herein shown and described, characterized particularly as to novelty by a vigorous upright growth habit, flower color in the Red Group 42B to 42D, seven leaflet leaves, large and small prickles on the lateral branches, prickles and glands on the petioles, and a reddish strip on the otherwise green styles.

* * * * *

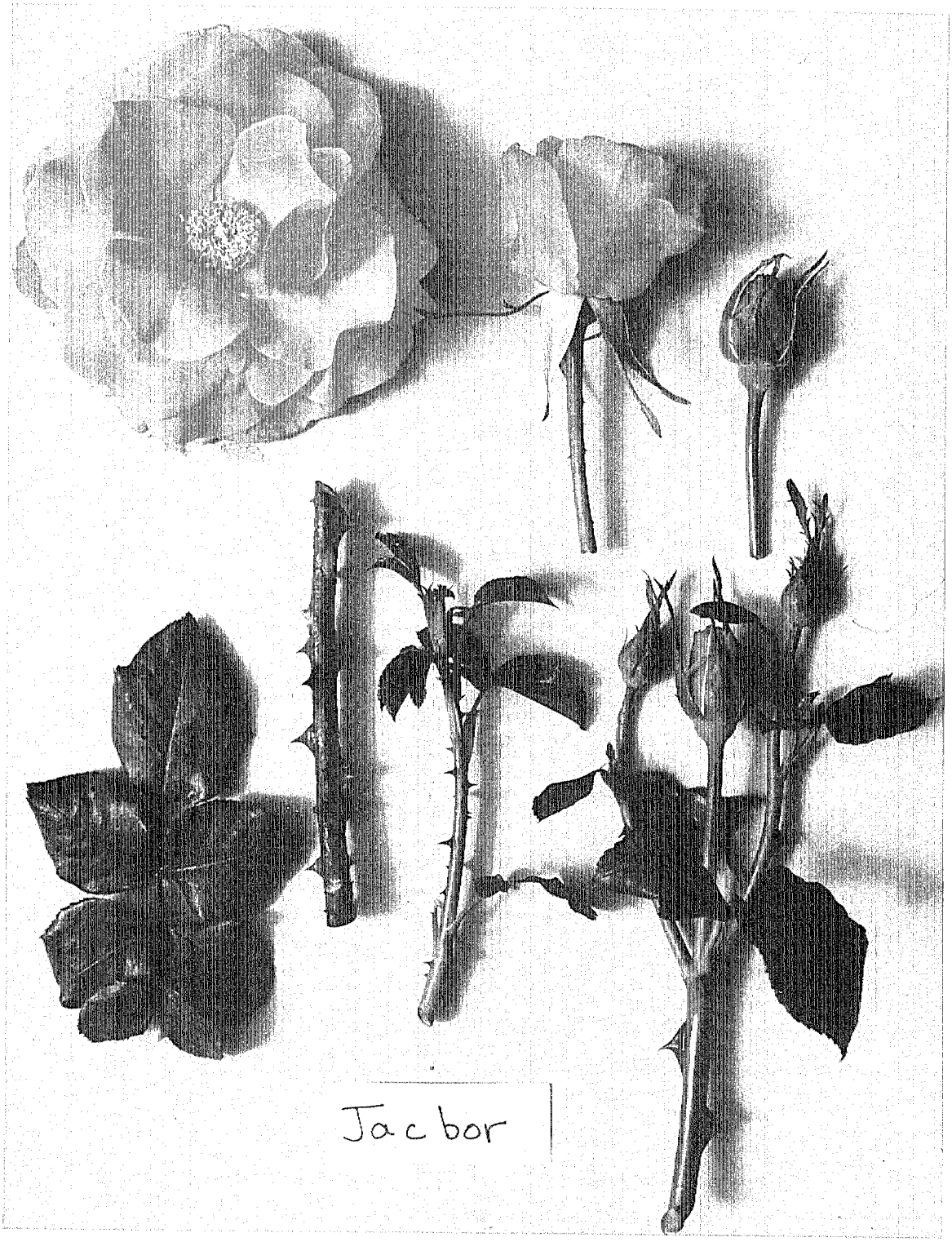
Jacbor